(12) United States Patent
Peterson et al.

(10) Patent No.: US 11,964,130 B2
(45) Date of Patent: Apr. 23, 2024

(54) IMPLANTABLE MEDICAL DEVICE WITH DRUG RESERVOIR VOLUME MEASUREMENT SYSTEM

(71) Applicant: Medtronic, Inc., Minneapolis, MN (US)

(72) Inventors: Erik J. Peterson, Fridley, MN (US); Jerel K. Mueller, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 623 days.

(21) Appl. No.: 17/134,989

(22) Filed: Dec. 28, 2020

(65) Prior Publication Data

US 2022/0203025 A1   Jun. 30, 2022

(51) Int. Cl.
   *A61M 5/168*   (2006.01)
   *A61M 5/142*   (2006.01)

(52) U.S. Cl.
   CPC ...... *A61M 5/1684* (2013.01); *A61M 5/14276* (2013.01); *A61M 2202/02* (2013.01); *A61M 2205/18* (2013.01); *A61M 2205/3331* (2013.01); *A61M 2205/3368* (2013.01); *A61M 2205/3379* (2013.01)

(58) Field of Classification Search
   CPC .................................................. A61M 5/1684
   See application file for complete search history.

(56) References Cited

U.S. PATENT DOCUMENTS

| | | | |
|---|---|---|---|
| 4,360,019 A | 11/1982 | Portner et al. | |
| 4,573,994 A | 3/1986 | Fischell et al. | |
| 4,772,263 A | 9/1988 | Dorman et al. | |
| 5,217,442 A | 6/1993 | Davis | |
| 6,283,943 B1 | 9/2001 | Dy et al. | |
| 6,579,280 B1 | 6/2003 | Kovach et al. | |
| 6,962,580 B2 | 11/2005 | Adams et al. | |
| 7,072,802 B2 | 7/2006 | Hartlaub | |
| 7,637,897 B2 | 12/2009 | Ginggen | |
| 7,942,863 B2 | 5/2011 | Kalpin et al. | |
| 9,122,785 B2 | 9/2015 | Alme et al. | |
| 9,421,325 B2 | 8/2016 | Kalpin | |
| 10,245,378 B2 | 4/2019 | Raman et al. | |

(Continued)

FOREIGN PATENT DOCUMENTS

WO   WO 2013/052414 A2   4/2013

OTHER PUBLICATIONS

Application and File history for U.S. Appl. No. 16/948,753, filed Sep. 30, 2020. Inventors: Peterson et al.

*Primary Examiner* — Jenna Zhang
(74) *Attorney, Agent, or Firm* — Husch Blackwell LLP

(57) ABSTRACT

An implantable medical device (IMD) including a housing defining a propellant chamber, a drug reservoir located within the propellant chamber of the housing configured to receive a therapeutic fluid, a propellant gas within the propellant chamber; and a volume measurement system that includes a temperature sensor configured to measure a temperature of the propellant gas within in the propellant chamber and a pressure sensor configured to measure a pressure of the propellant gas within the propellant chamber. The volume measurement system is configured to measure the pressure and the temperature of the propellant gas to provide current volume information of the therapeutic fluid in the drug reservoir.

23 Claims, 4 Drawing Sheets

(56) References Cited

U.S. PATENT DOCUMENTS

| | | | |
|---|---|---|---|
| 2005/0277974 A1* | 12/2005 | Hassler | A61F 2/004 606/151 |
| 2006/0089619 A1 | 4/2006 | Ginggen | |
| 2006/0089620 A1 | 4/2006 | Gibson et al. | |
| 2008/0243093 A1 | 10/2008 | Kalpin et al. | |
| 2011/0254686 A1* | 10/2011 | Kalpin | A61M 5/1684 604/93.01 |
| 2011/0301575 A1 | 12/2011 | Miesel et al. | |
| 2013/0116665 A1 | 5/2013 | Humayun et al. | |
| 2014/0228765 A1 | 8/2014 | Burke et al. | |
| 2017/0043151 A1 | 2/2017 | Bellrichard et al. | |
| 2018/0214635 A1* | 8/2018 | Raman | A61M 5/172 |
| 2020/0121850 A1* | 4/2020 | Christenson | A61M 5/1413 |
| 2022/0096738 A1 | 3/2022 | Peterson et al. | |

* cited by examiner

IMPLANTABLE MEDICAL DEVICE WITH DRUG RESERVOIR VOLUME MEASUREMENT SYSTEM

TECHNICAL FIELD

The present application relates to medical devices that include expandable drug reservoirs and techniques to determine the drug reservoir volume of such devices.

BACKGROUND

A variety of medical devices are used for acute, chronic, or long-term delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, drug infusion pumps or other fluid delivery devices can be used for chronic delivery of therapeutic agents. Typically, such devices provide therapy continuously or periodically according to programmed parameters. The programmed parameters can specify a therapeutic regimen (e.g., the rate, quantity, and timing of medicament delivery to a patient), as well as other functions of the medical device.

Implantable medical devices such as drug pumps are typically implanted at a location within the body of a patient (typically a subcutaneous region in the lower abdomen) and are configured to deliver a therapeutic fluid through a catheter to a target treatment site. Drug pumps typically include a drug reservoir and pumping mechanism that deliver a fluid containing a pharmaceutical agent to the patient via a catheter under a set schedule over an extended period of time to the target treatment site. The catheter used in these devices is generally configured as a flexible tube with a lumen running the length of the catheter that transports the therapeutic fluid.

Implantable medical devices can have refillable drug reservoirs for housing therapeutic fluids that are periodically refilled so that the implanted device can be employed for chronic long-term use. A refill apparatus or needle can be percutaneously inserted into an injection port of the device that is in communication with the drug reservoir to provide fresh therapeutic fluid. Ascertaining the current volume information of the drug reservoir, e.g., the relative fullness, may be useful during refill procedures or for determining whether the device is functioning properly.

Accurately determining the current volume information of the drug reservoir may be challenging and may often require labor or time intensive methods. For example, during refill, the residual supply of therapeutic fluid in a drug reservoir may be determined by evacuating, or aspirating, to the extent possible, the residual supply of therapeutic fluid in the reservoir using a syringe, and determining the volume of the remaining therapeutic fluid from the graduations on the syringe. Such procedure may be described as being wasteful and invasive for the patient.

In some conventional systems, the present volume level within a drug reservoir is estimated based on the number of cycles implemented by the pumping mechanism of the device. Under a scheduled regimen, the device may be configured to pump or deliver a select amount of fluid from the drug reservoir to the target treatment site. The system is thus programmed to deliver a select amount of therapeutic fluid to the patient with each cycle of the pump mechanism. Knowing the number of cycles that the pump mechanism undergoes provides an estimate of the fluid delivered to the patient and, in turn, an estimate of the current volume information of the drug reservoir. However, pressure differentials within the system created by, for example, restrictions within a catheter, variations induced by the pumping mechanism, leaks within the system, and similar complications are generally not accounted for with such mechanisms. Thus, the difference between the actual amount of fluid remaining within the drug reservoir and the anticipated amount remaining may be substantially different. Further, such accounting mechanisms fail to analyze the amount of fluid introduced during a refill procedure.

SUMMARY

Embodiments of the present disclosure provide a system and method to measure the current reservoir volume information an implantable medical device. The disclosed systems use a volume measurement system to monitor the temperature and pressure of the propellant gas within the propellant chamber to determine a current volume of propellant gas. As the volume of the drug reservoir changes during use, the corresponding volume of the propellant gas will likewise change. For example, as the volume of therapeutic fluid decreases during use, the volume of propellant gas within the propellant chamber will increase. With knowledge of the volume of propellant gas, the volume of the drug reservoir can be determined allowing the current volume information of the drug reservoir to be determined.

In an embodiment, the disclosure describes an implantable medical device including a housing defining a propellant chamber therein; a drug reservoir located within the propellant chamber of the housing configured to receive a therapeutic fluid therein; a propellant gas within the propellant chamber; and a volume measurement system that includes a temperature sensor configured to measure a temperature of the propellant gas within in the propellant chamber; a pressure sensor configured to measure a pressure of the propellant gas within the propellant chamber, where the volume measurement system is configured to measure the pressure and the temperature of the propellant gas to provide current volume information of the therapeutic fluid in the drug reservoir.

In another embodiment, the disclosure describes a method of producing an implantable medical device comprising a volume measurement system, the method includes providing an implantable medical device having a housing that defines a propellant chamber, and a drug reservoir positioned within the propellant chamber; installing a volume measurement system in the implantable medical device, the volume measurement system comprising a temperature sensor configured to measure a temperature of a propellant gas within in the propellant chamber and a pressure sensor configured to measure a pressure of the propellant gas within the propellant chamber; charging the propellant chamber with a positive gauge pressure of a propellant gas; and calibrating the volume measurement system so that the volume measurement system is configured to measure the pressure and the temperature of the propellant gas to provide current volume information of the therapeutic fluid in the drug reservoir.

In another embodiment, the disclosure describes a method of determining a reservoir volume information of an implantable medical device. The method includes providing an implantable medical device having a housing that defines a propellant chamber, and a drug reservoir positioned within the propellant chamber, a propellant gas within the propellant chamber, a volume measurement system comprising a temperature sensor and a pressure sensor, and processing circuitry connected to the volume measurement system;

measuring, using the processing circuitry, a current temperature of the propellant gas in the propellant chamber with the temperature sensor; measuring, using the processing circuitry, a current pressure of the propellant gas in the propellant chamber with the pressure sensor; and determining, using the processing circuitry, current volume information of a therapeutic fluid in the drug reservoir based on the current temperature and the current pressure of the propellant gas in the propellant chamber.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which:

FIG. 2A shows the drug reservoir in a near full configuration and FIG. 2B shows the drug reservoir in a more depleted configuration.

Figure 1:
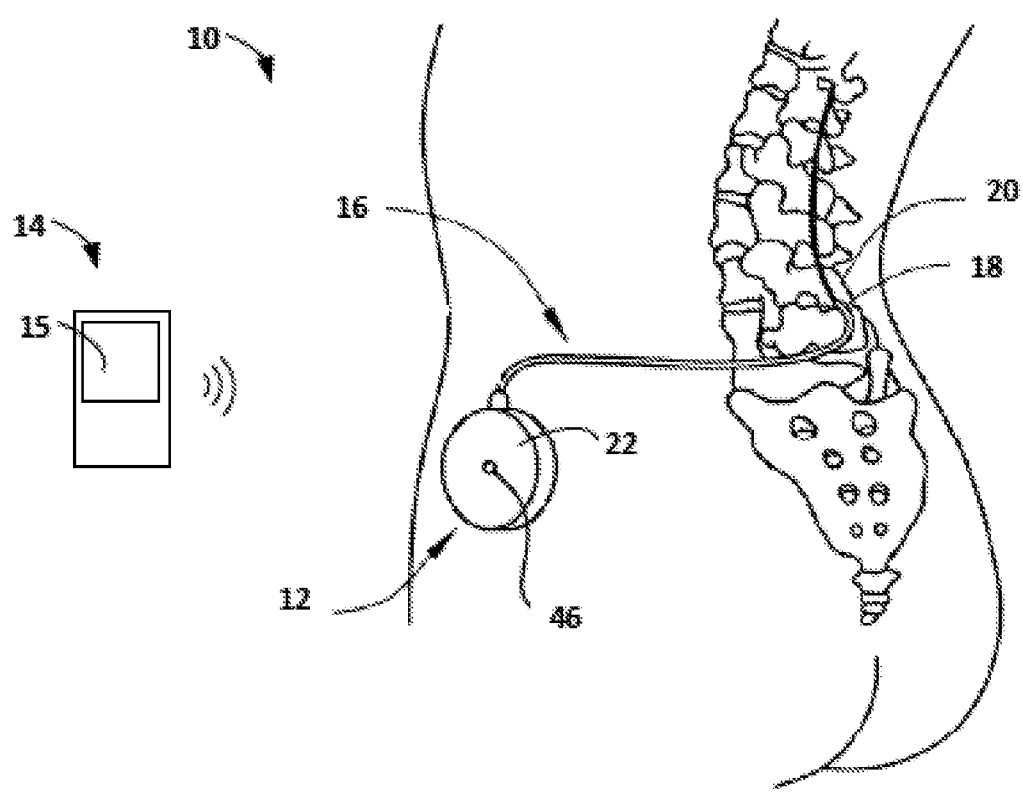
FIG. 1 is schematic view showing an exemplary drug infusion system including an external device and an implantable medical device containing the disclosed volume measurement system implanted in a patient.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 is schematic view showing an exemplary drug infusion system 10 including an implantable medical device 12 illustrated as an implantable drug pump implanted in a patient and an external device 14 configured to wirelessly communicate with implanted medical device 12. Infusion system 10 also includes catheter 16, which may include an elastomeric tube, coupled to implantable medical device 12 and configured to transport a therapeutic fluid from implantable medical device 12 to a target treatment site 18 under a set drug regimen established by the processing circuitry of implantable medical device 12.

Implantable medical device 12 may be surgically implanted in any suitable location, such as subcutaneously in the pectoral, abdominal, or other region of the body of the patient. The target treatment site 18 may be any suitable location within the body of the patient such as within the intrathecal space along the spinal canal 20 of the patient as shown in FIG. 1, the blood stream, the stomach, the cranium, the heart, or other suitable location.

As discussed further below, implantable medical device 12 may include processing circuitry configured to wirelessly communicate with external device 14 to allow for monitoring or adjustments to the programing of implantable medical device 12 as well as assessment of the current volume information of the drug reservoir within implantable medical device 12.

External device 14 may include a display 15 for presenting information to a user, such as a healthcare provider or a patient. In one or more embodiments, external device 14 is capable of presenting volume information, using the display 15 or another output device, to the user regarding the drug reservoir. Such volume information may include, but is not limited to, the current volume of the therapeutic fluid remaining or located within the drug reservoir, the volume capacity of the therapeutic fluid remaining (e.g., relative percentage remaining), the number of doses remaining, the duration of remaining doses within the drug reservoir (e.g., number of days or weeks before the drug reservoir is depleted), and the like. In some embodiments, external device 14 may be capable of presenting alerts, or notifications via display 15 or another output device to indicate to the user that the volume information regarding the therapeutic fluid within the drug reservoir of implantable medical device 12, such as whether the device has reached a particular capacity or threshold value. For example, the external device 14 may provide an alert, or notification, to a user when the drug reservoir contains less than a preset threshold value such as a lower threshold volume of prescribed therapeutic fluid (e.g., less than 10% total capacity or some other value), a threshold number of remaining therapeutic doses, or a threshold duration of remaining therapeutic doses (e.g., less than a week left of prescribed doses of the therapeutic fluid or other duration).

Any suitable external device 14, such as a programmer (e.g., a MEDTRONIC, INC. N'VISION clinician programmer or a MEDTRONIC, INC. MYP™ patient programmer), a tablet computer, a smart phone, a personal data assistant, a laptop computer, or the like, may be employed, provided that it can communicate with implantable medical device 12. In some embodiments external device 14 may include a cellular telephone, tablet, or desktop computer with an associated monitor serving as display 15. In order for a person to interact with external device 14, external device 14 may include a user interface coupled to the computing apparatus. The user interface may include a touchscreen, a keyboard, graphical user interface, and/or combinations thereof.

In some embodiments, display 15 may be touchscreen that may allow a user to view and/or manipulate data on display 15 and allow a user to interact with implantable medical device 12. External device 14 may further include a speaker for broadcasting audible tones or messages used to communicate with a user regarding, e.g., vocalizations of volumes, alerts, alarms, notifications, etc. External device 14 may further include a communications module or other functionality used for transferring data (e.g., over the internet, over a network, etc.) to a central database or communicating with patient management systems.

External device 14 may be a microprocessor-controlled device, and thus, may include computing apparatus that includes one or more microprocessors that operate with associated memory for controlling various processes and functions of external device 14 including initiating one or more volume measurements using implantable medical device 12, wirelessly transferring data and commands between implantable medical device 12 and external device 14, issuing alerts, or notifications based on the current volume information of the drug reservoir of implantable medical device 12, detecting the pressure and temperature within the propellant chamber and calculating a current volume information of the drug reservoir based on such information. Still further, external device 14 may be further configured to store data from implantable medical device 12 such as, the drug reservoir volume data over time, average flow rates, sensor system diagnostics, volume discrepancies (e.g. with respect to programmed expectations) for various time durations, events where volume changes exceed selected thresholds, etc.

External device 14 may include a telemetry circuit and an antenna for bidirectional communication with implantable medical device 12. Data and commands may be transmitted and received during uplink or downlink telemetry between implantable medical device 12 and external device 14 using the telemetry circuit and the antenna. The wireless operable coupling between implantable medical device 12 and external device 14 may use one or more wireless (e.g., radio frequency) data transmission protocols such as, e.g., BLUETOOTH, WI-FI, Medical Implant Communications Service (MICS), any protocol in the ultra-high frequency (UHF) band, any protocol in the super high frequency (SHF) band, low frequencies, etc.

Figure 2A:
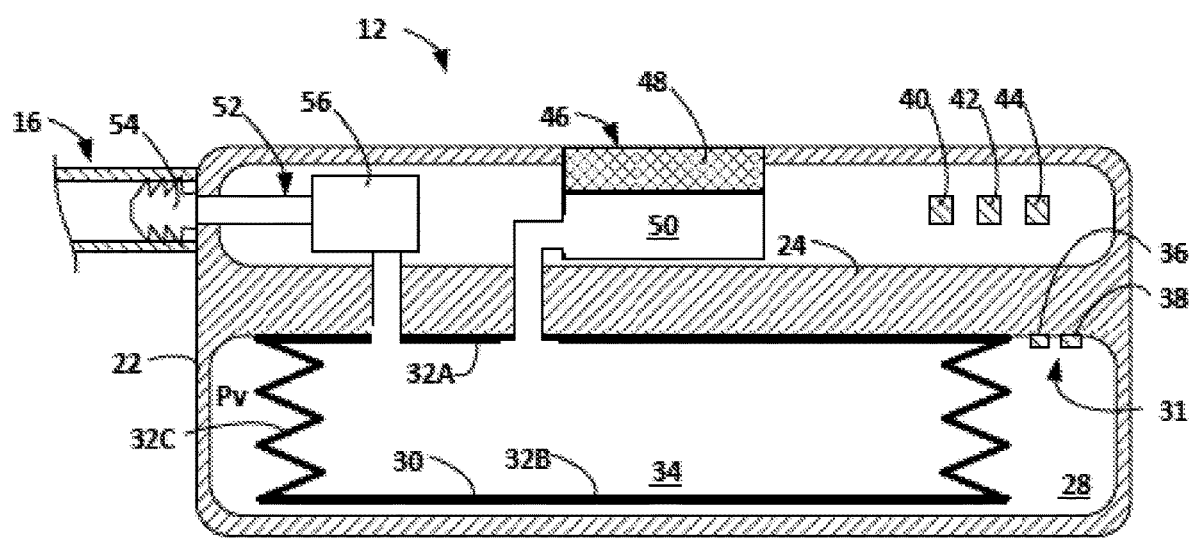
FIGS. 2A and 2B are schematic cross-sectional views of an exemplary implantable medical device such as the one shown in FIG. 1 including the disclosed volume measurement system.
Figure 2B:
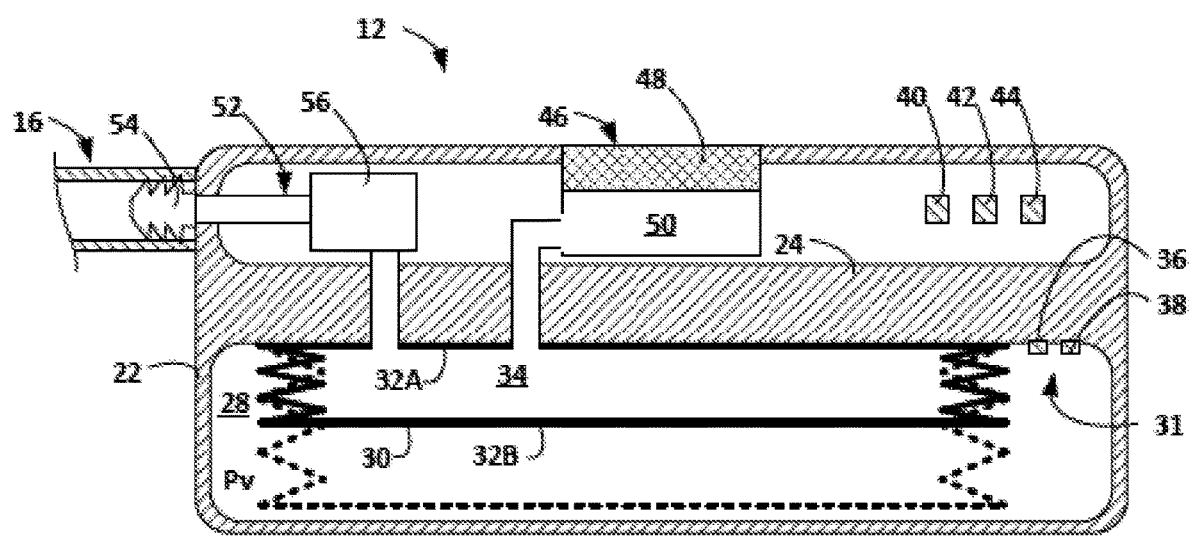

FIGS. 2A and 2B are schematic cross-sectional views of an example implantable medical device 12 that may be used with system 10 in FIG. 1 illustrating select internal features of the device. FIG. 2A illustrates drug reservoir 30 in a near-full configuration while FIG. 2B illustrates drug reservoir 30 in a more depleted configuration. Although device 12 is generally described herein in relation to an implantable drug pump, the disclosed volume measurement systems of the present disclosure may be utilized with other types of drug delivery devices such as ambulatory or wearable infusion pumps.

As shown in FIGS. 2A and 2B, implantable medical device 12 includes a housing 22 with a bulkhead 24 that divides an interior space of housing 22 into two or more chambers. The interior space of housing 22 includes a propellant chamber 28 that is at least partially defined by bulkhead 24. Expandable drug reservoir 30 is housed within propellant chamber 28 and receives the therapeutic fluid, which is then administered to the patient under a set drug regimen. Bulkhead 24 may help separate or hermetically seal propellant chamber 28 and expandable drug reservoir 30 from other components contained in implantable medical device 12. Although certain examples are described with respect to expandable drug reservoir 30, in other examples, the reservoir may not be expandable.

In some embodiments, expandable drug reservoir 30 may include an accordion- or bellows-style reservoir that includes a first side 32A and second side 32B opposite of first side 32A. First and second sides 32A and 32B may be connected by collapsible side 32C which forms the perimeter of expandable drug reservoir 30. Collectively, the sides of drug reservoir 30 define an enclosed space containing reservoir volume 34. Side 32C may define an accordion fold to allow the side to expand or collapse with changes in the drug reservoir volume.

In some embodiments, first and second sides 32A and 32B of drug reservoir 30 may be described as rigid, or resilient, so as to be resistant to deflection. For example, in this embodiment, second side 32B may lie in plane, or be planar, and may resist deflection out of the plane and move as a single element, e.g., towards and away from bulkhead 24. More specifically, second side 32B may be described as moving substantially linearly along an axis that is perpendicular to the plane of the side. In other words, second side 32B may be described as moving orthogonally to the plane that second side 32B lies within. In some embodiments, device 12 may also include an optional guide mechanism used in conjunction with drug reservoir 30 to maintain proper alignment of second side 32B as it transitions from full to a depleted configuration.

In the illustration shown in FIGS. 2A and 2B, first side 32A is positioned and attached to bulkhead 24 allowing second side 32B to move relative to first side 32A with changing therapeutic fluid volume. It will be understood, however, that drug reservoirs other than bellows-type reservoirs may be employed using the exemplary systems, apparatus, devices, and methods described herein. While the below description is based primarily on the structural arrangement of drug reservoir 30, the utility of volume measurement 31 does not need to be limited to a particular type of drug reservoir. In other embodiments, drug reservoir 30 may include a bladder-style reservoir with flexible sides, reservoirs with asymmetric shapes, and/or those having non-defined shapes. The volume measurement system 31 may work with different types of drug reservoirs 30 including those with flexible sides, asymmetric or non-defined shapes that make it difficult to measure the internal volume of drug reservoir 30 based on geometry alone.

Expandable drug reservoir 30 expands from a depleted configuration to a full configuration based on the receipt and amount of therapeutic fluid introduced into reservoir volume 34. In some embodiments, collapsible side 32C of expandable drug reservoir 30 may be a collapsible accordion-style or bellows-style cylindrical side wall that allows at least one of first or second side 32A or 32B to move with the change of volume. When in the full configuration, first side 32A and second side 32B will be at a maximum separation distance from each other. At max separation, the volume of propellant gas (Pv) within propellant chamber 28 will be at its minimum. In contrast, in the depleted configuration, first side 32A and second side 32B will be at a minimum separation distance from each other. In the minimum drug reservoir volume configuration, the volume of propellant gas (Pv) within propellant chamber 28 will be at its maximum.

Drug reservoir 30 may be constructed of any suitable material. In some embodiments, sides 32A-32C of drug reservoir 30 may be made of a nonferromagnetic metal such as titanium, a rigid polymeric material or composite, or the like. In some embodiments, drug reservoir 30 may be a bellows-style titanium drug reservoir.

Propellant chamber 28 includes a propellant gas (Pv) disposed outside of drug reservoir 30 and reservoir volume 34 but inside housing 22 so as to at least partially surround drug reservoir 30. The propellant gas (Pv) exerts a pressure on at least a portion of expandable drug reservoir 30 such that the pressure reservoir volume 34 is positive at all volumes between the expanded and collapsed states. The propellant gas acts as a pressure-providing means to propellant chamber 28 and drug reservoir 30. When therapeutic fluid is removed from drug reservoir 30 (e.g., to delivered to the patient, to be removed from the pump by a clinician, etc.), the pressure exerted on drug reservoir 30 by the propellant (Pv) may assist in fluid exiting from device 12. More specifically, drug reservoir 30 may contract due to the therapeutic fluid exiting from drug reservoir 30 and the pressure exerted on the exterior of drug reservoir 30 by the propellant (Pv). The propellant gas (Pv) employed in examples of implantable medical device 12 may comprise at least one of butane, perfluorohexane, or perfluoropentane. Other gases may also be used in alternative embodiments.

During refill procedures or the general administration of therapeutic fluid from implantable medical device 12 it may be important to accurately know the amount of therapeutic fluid contained within expandable drug reservoir 30. Tracking of the volume information (e.g., the relative fullness of drug reservoir 30) may be important to understand if any leaks or occlusions within the infusion system 10 have occurred, whether device 12 is malfunctioning, whether proper refilling of device 12 has occurred, as well as a number of other properties of the device.

The disclosed implantable medical device 12 provides a mechanism for accurately determining the current volume information of drug reservoir 30 by using a volume measurement system 31 that includes a temperature sensor 36 and a pressure sensor 38 positioned within propellant chamber 28. Volume measurement system 31 is configured to determine current volume information of the fluid in drug reservoir 30 based on the current volume of the propellant gas (Pv) within propellant chamber 28 using the current temperature and pressure of the propellant gas.

In some embodiments, the volume of the propellant gas (Pv) may be determined based on the ideal gas law solved for volume which is shown in Equation 1.

$$V_{Pv} = \frac{nRT}{P} \qquad \text{Equation 1}$$

Where $V_{Pv}$ is the volume of the propellant gas, n is the amount of gas within the propellant chamber 28, R is the universal gas constant (e.g., 8.314 J/(K·mol)), T is the temperature within the propellant gas within propellant chamber 28, and P is the pressure within propellant chamber 28.

The volume of the fluid within drug reservoir 30 may then be determined based on Equation 2.

$$V_T = V_{Pv} + V_{DR} \qquad \text{Equation 2}$$

Where $V_T$ is the total fluid volume within propellant chamber 28 including the volume of fluid within drug reservoir 30 ($V_{DR}$). $V_T$ is a fixed amount for a given medical device 12.

While it is possible to determine n for a given medical device during manufacturing, variations from one device to another may make it difficult and costly to determine n for each medical device under production. Further, while the universal gas constant R provides a good theoretical estimation for calculating the volume within propellant chamber 28, selection of propellant gas or fluctuations in propellant gas composition can lead to variation in the calculated volume for the propellant gas (Pv). To provide a more accurate determination of the propellant gas volume, during manufacturing device 12 may undergo a simple calibration procedure where the volume of the propellant gas is determined as a function of pressure and temperature within propellant chamber 28 as indicated by Equation 3.

$$V_{Pv} = f(P, T) = A\frac{T}{P} \qquad \text{Equation 3}$$

Where A is an empirically measured constant for a given device 12 determined through calibration of the device having SI units of J·K$^{-1}$. It will be understood that the units are used merely to convey the proper information. The measured calibration constants can be easily converted into any relevant values (e.g., temperature in Fahrenheit, Celsius, or the like) to relay desirable information to the user. Thus, regardless of how the information and values are stored or relayed, the SI units of the disclosed constants will be recognized as remaining the same. In an ideal scenario, A is equal to nR, but in reality, may vary slightly depending on selection of propellant and whether it is fully in the gaseous state or partially liquid. By measuring A empirically, the effect on the volume calculation for the propellant gas based on variability between the amount of gas n introduced into propellant chamber 28 and the environmental conditions under which it is introduced or any variations generated in the composition of the propellant gas can be minimized or negated.

Equations 2 and 3 can be combined and solved for the fluid volume $V_{Dr}$ within drug reservoir 30 as shown in Equation 4.

$$V_{Dr} = V_T - A\frac{T}{P} \qquad \text{Equation 4}$$

Where $V_T$ and A are constants for a given medical device 12. $V_T$ is the volume constant having SI units of m$^3$ and A is the measured gas calibration constant for the propellant gas of having SI units of J·K$^{-1}$.

The calibration constant A, and optionally constant $V_T$, can be measured for a given medical device by calibrating device 12 using for example, a two-point calibration. $V_T$ may be known as part of the device design parameters and/or determined as part of the calibration. A and $V_T$ can be stored for a given medical device 12 in the memory of the device. The calibration can be carried out using known amounts of different volumes of a calibration fluid introduced intro drug reservoir 30 and measuring the temperature and pressure using sensors 36 and 38 respectively.

In some embodiments, the two known sample amounts of fluid may be sufficient to create a substantially full (e.g., full or nearly full) and a substantially depleted (e.g., emptied or nearly emptied) configuration in drug reservoir 30. Equation 4 may then be used during routine operation using the stored constants and real-time measurements of T and P to determine the present fluid volume ($V_{Dr}$) within drug reservoir 30 and any other relevant volume information (e.g., volume capacity, remaining duration of operation, and the like).

The configuration of volume measurement system 31 allows for the simple determination of the fluid volume within drug reservoir 30 without needing to include any additional moving parts or modify the components in direct contact with the therapeutic fluid. Thus, additional testing or consideration of whether volume measurement 31 will contribute to the degradation or long-term stability of the therapeutic fluid within drug reservoir 30 is not needed as might be needed with other volume measurement systems that require direct contact with the therapeutic fluid or exposure of the fluid to electromagnetic radiation or mechanical effects like ultrasound. Further variations in the type of therapeutic fluid introduced into drug reservoir will not impact the accuracy of volume measurement system 31.

Temperature sensor 36 may include any suitable device such as a thermostat or thermocouple sensor mounted within device such that the sensor is configured to measure the temperature of propellant gas (Pv) within propellant chamber 28. In some embodiments, temperature sensor 36 may be mounted at a location within propellant chamber 28 so that the sensor is substantially isolated from other electrical components that may produce local hot spots and contribute to inaccuracies in the temperature reading. Additionally, in some examples, device 12 may include a plurality of temperature sensors 36 for purposes of redundancy.

Pressure sensor 38 includes any suitable device configured to measure the pressure within propellant chamber 28. Example sensors may include, but are not limited to, MEMS pressure sensors, capacitive pressure transducers, diaphragm sensors, and the like. The pressure within propellant chamber 28 may always be positive relative to the external environment (e.g., positive gauge pressure) so that the propellant gas (Pv) provides a driving force for evacuating drug reservoir 30. Additionally, in some examples, device 12 may include a plurality of temperature pressure sensors 38 for purposes of redundancy.

Implantable medical device 12 also includes other components such as processing circuitry 40, telemetry circuit 42, and power source 44 to power and control the various components implantable medical device 12. Both temperature and pressure sensors 36 and 38 may be electrically coupled and operated by to processing circuitry 40. Processing circuitry 40 may include one or more microprocessors that operate with associated memory for controlling various processes and functions of the implantable medical device 12 including the various components of volume measurement system 31 and pump mechanism 56. Telemetry circuitry 42 may include an antenna, and may be configured to be used with processing circuitry 40 to transmit and receive data and commands during uplink or downlink telemetry between device 12 and external device 14 to provide wireless operable coupling between implantable medical device 12 and external device 14 via suitable wireless data transmission protocols such as, e.g., BLUETOOTH, WI-FI, Medical Implant Communications Service (MICS), any protocol in the ultra-high frequency (UHF) band, any protocol in the super high frequency (SHF) band, low frequencies, etc.

Implantable medical device 12 further includes an injection port 46 through which a needle of a refill kit, may enter to refill drug reservoir 30. Injection port 46 may include a self-sealing, needle-penetrable septum 48 to allow access to refill chamber 50 that is in fluid communication with reservoir volume 34 of drug reservoir 30. While not shown in FIGS. 2A and 2B, injection port 46 may include other useful features such as a prefilter, flow valves, or other components that may be useful in such systems.

Implantable medical device also includes outlet port 52 in fluid communication with reservoir volume 34 of drug reservoir 30. Outlet port 52 may include a suitable catheter connector 54 such as a barb-style connector configured to couple with the proximal end of treatment catheter 16 during an implantation procedure. Implantable medical device 12 may also include, or contain, a catheter injection port in communication with catheter 16 at a location downstream of drug reservoir 30 for sampling fluid.

Implantable medical device 12 may include an optional pumping mechanism 56 or structure capable of delivering one or more fluids from drug reservoir 30 to target treatment site 18 under a scheduled regimen. In some embodiments pumping mechanism 56 may be powered by power source 44 and processing circuitry 40 (e.g., piston pumps, diaphragm pumps, peristaltic pumps, etc.), may be driven in part based on pressure provided by propellant gas (Pv) (e.g., positive pressure to collapse drug reservoir 30), or combinations thereof.

In some embodiments, operation of device 12 may be controlled and monitored by processing circuitry 40 to track the cycles undergone by pumping mechanism 56 during operation to determine an anticipated volume information of drug reservoir 30 at any given point in time. The anticipated volume information can then be compared to current volume information provided by volume measurement system 31 to provide useful information regarding the function of system 10. For example, relative consistency between the two determinations (e.g., anticipated vs current volume information) may indicate normal operation of system 10. However, if the anticipated volume information is lower than the current volume information determined by volume measurement system 31, system 10 may indicate to the user that a higher level of therapeutic fluid remains in drug reservoir 30 than anticipated, which may be an indication of possible occlusion somewhere within system 10. Likewise, if the anticipated volume information is higher than the current volume information determined by volume measurement system 31, system 10 may indicate to the user that a lower level of therapeutic fluid remains in drug reservoir 30 than anticipated, which may be an indication of possible leaks or other malfunctions within system 10. In either scenario, implantable medical device 12 may send a signal to external device 14 to alert the user of possible complications with system 10.

The sampling rate of volume measurement 31 may set to balance power usage and activity demands. For example, in situations that require a higher rate of sampling, e.g., during refill procedures, volume measurement system 31 may be set to transmit and receive signal 106 on the order of every second to monitor the filling process. During routine operation, a lower rate of sampling may be used, on the order of hourly, daily, or the like to preserve battery life while also provided useful feedback regarding the current volume information of drug reservoir 30. Additionally, or alternatively, the sampling rate may coincide with the drug delivery rate. For example, systems with higher drug delivery rates may sample more often compared to systems with lower drug delivery rates.

Figure 3:
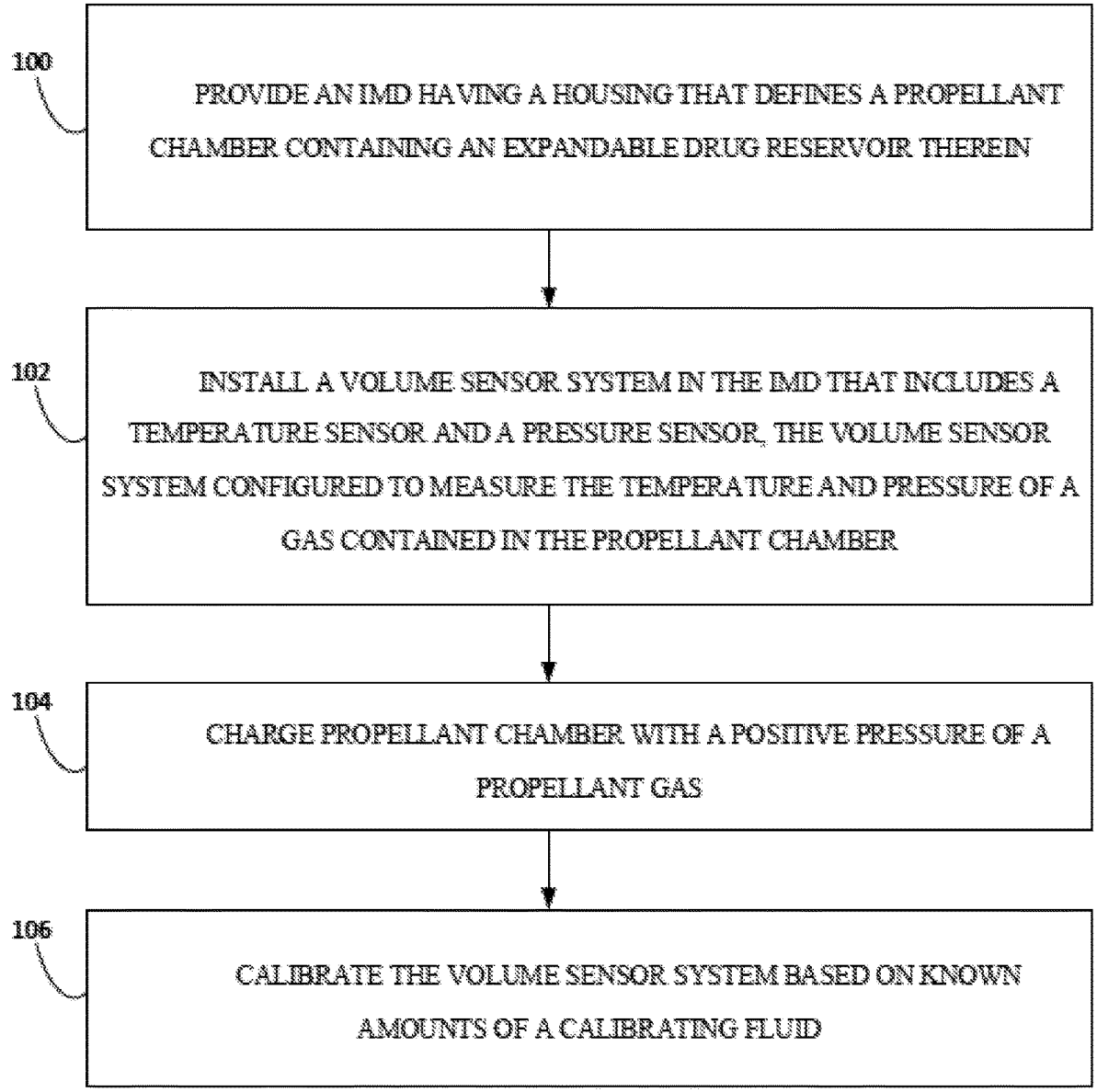
FIG. 3 is a flow diagram of a method for calibrating the disclosed volume measurement system.

FIG. 3 is a flow diagram of a method of producing and calibrating volume measurement 31 of implantable medical device 12. For simplicity, the method of FIG. 3 is described with respect to volume measurement systems 31. However, the method may be applied or adapted for use with the other disclosed volume measurement systems or the disclosed volume measurement system may be produced and calibrated using other methods than those disclosed by FIG. 3.

The method of FIG. 3 includes providing an implantable medical device 12 having a housing 22 that defines a propellant chamber 28 that includes an expandable drug reservoir 30 (100); installing a volume measurement system 31 in the implantable medical device that includes temperature sensor 36 and pressure sensor 38 within propellant chamber 28 configured to measure the temperature and pressure of a gas contained therein (102); charging propellant chamber 28 with a positive pressure of a propellant gas (104); calibrating volume measurement system 31 based on known amounts of calibrating fluid (106).

As discussed above, calibrating volume measurement system 31 may be done using at least a two-point calibration procedure that includes using known amounts of a calibrating fluid, using Equation 4, and measuring the temperature and pressure of propellant gas (Pv). The amounts of calibration fluid may be sufficient to establish a substantially full and substantially depleted configuration within drug reservoir 30. For the substantially depleted configuration, calibrating fluid may be flushed through drug reservoir 30 and device 12 to purge any residual air within the device. Drug reservoir 30 may then be fully collapsed resembling a depleted or zero-volume configuration. In such examples, the zero-volume configuration may still include residual amounts of calibration fluid however, because the device is essentially evacuated, the known amount of fluid for calibration purposes may be considered zero. The calibration procedure may be used to determine calibration constant A, and optionally $V_T$, which can then be stored in the memory of device 12 and used in conjunction with Equation 4 to determine current fluid volume information in drug reservoir 30.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An implantable medical device comprising:
    a housing defining a propellant chamber therein;
    a drug reservoir located within the propellant chamber of the housing configured to receive a therapeutic fluid therein;
    a propellant gas within the propellant chamber; and
    a volume measurement system comprising:
        a temperature sensor configured to measure a temperature of the propellant gas within the propellant chamber;
        a pressure sensor configured to measure a pressure of the propellant gas within the propellant chamber, wherein the volume measurement system is configured to measure the pressure and the temperature of the propellant gas to provide current volume information of the therapeutic fluid in the drug reservoir, and without requiring direct contact of the therapeutic fluid with the temperature sensor.

2. The implantable medical device of claim 1, wherein the volume measurement system is configured to measure the current volume of the therapeutic fluid based on the current volume of the propellant gas using the temperature and the pressure measured by the temperature sensor and the pressure sensor.

3. The implantable medical device of claim 2, wherein the current volume of the propellant gas is determined based on a function of an ideal gas law.

4. The implantable medical device of claim 1, wherein the propellant gas comprises butane, perfluorohexane, or perfluoropentane.

5. The implantable medical device of claim 1, wherein the propellant gas provides a positive gauge pressure in the propellant chamber.

6. The implantable medical device of claim 1, wherein the device is configured to send an alert to an external device in response to the current volume information of the therapeutic fluid in the drug reservoir reaching a predetermined threshold.

7. The implantable medical device of claim 6, wherein the predetermined threshold is indicative of a number of therapeutic doses remaining or a duration of therapeutic doses remaining.

8. The implantable medical device of claim 1, further comprising a pump mechanism that cycles as the therapeutic fluid exits the drug reservoir under a predetermined regimen, wherein the pump mechanism is configured to determine an anticipated volume information based on the number of cycles, and wherein the device is configured to send an alert to an external device in response to the implantable medical device detecting a discrepancy between the current volume information determined by the volume measurement system and the anticipated volume information determined by the pump mechanism.

9. The implantable medical device of claim 1, wherein the drug reservoir is expandable.

10. The implantable medical device of claim 1, wherein the drug reservoir comprises collapsible titanium bellows.

11. The implantable medical device of claim 1, wherein the volume measurement system is configured to measure the pressure and the temperature of the propellant gas to provide current volume information of the therapeutic fluid in the drug reservoir without requiring direct contact of the therapeutic fluid with the pressure sensor.

12. An implantable medical device comprising:
    a housing defining a propellant chamber therein;
    a drug reservoir located within the propellant chamber of the housing configured to receive a therapeutic fluid therein;
    a propellant gas within the propellant chamber; and
    a volume measurement system comprising:
        a temperature sensor configured to measure a temperature of the propellant gas within the propellant chamber;

a pressure sensor configured to measure a pressure of the propellant gas within the propellant chamber, wherein the volume measurement system is configured to measure the pressure and the temperature of the propellant gas to provide current volume information of the therapeutic fluid in the drug reservoir, and is configured to measure the current volume of the therapeutic fluid based on Equation 4 below:

$$V_{Dr} = V_T - A\frac{T}{P} \quad \text{Equation 4}$$

wherein $V_{Dr}$ is the current volume of the therapeutic fluid having SI units of $m^3$, T is the temperature of propellant gas measured by the temperature sensor having SI units of K, P is the pressure of propellant gas measured by the pressure sensor having SI units of $J \cdot m^{-3}$, $V_T$ is a volume constant of the propellant chamber having SI units of $m^3$, and A is a gas constant of having SI units of $J \cdot K^{-1}$.

13. A method of producing an implantable medical device comprising a volume measurement system, the method comprising:
providing an implantable medical device comprising a housing that defines a propellant chamber, and a drug reservoir positioned within the propellant chamber;
installing a volume measurement system in the implantable medical device, the volume measurement system comprising a temperature sensor configured to measure a temperature of a propellant gas within the propellant chamber and a pressure sensor configured to measure a pressure of the propellant gas within the propellant chamber;
charging the propellant chamber with a positive gauge pressure of the propellant gas; and
calibrating the volume measurement system so that the volume measurement system is configured to measure the pressure and the temperature of the propellant gas to provide current volume information of the therapeutic fluid in the drug reservoir, and without requiring direct contact of the therapeutic fluid with the temperature sensor.

14. The method of claim 13, wherein calibrating the volume measurement system comprises using at least a two-point calibration procedure based on at least two known amounts of a calibrating fluid being introduced into the drug reservoir.

15. The method of claim 13, wherein the volume measurement system is configured to measure the current volume of the therapeutic fluid based on the current volume of the propellant gas using the temperature and the pressure measured by the temperature sensor and the pressure sensor, and wherein the current volume of the propellant gas is determined based on an ideal gas law.

16. The method of claim 13, wherein the propellant gas comprises butane, perfluorohexane, or perfluoropentane.

17. The method of claim 13, wherein the device is configured to send an alert to an external device in response to the current volume information of the therapeutic fluid in the drug reservoir reaching a predetermined threshold.

18. The method of claim 17, wherein the predetermined threshold is indicative of a number of therapeutic doses remaining or a duration of therapeutic doses remaining.

19. The method of claim 13, wherein the volume measurement system is configured to measure the pressure and the temperature of the propellant gas to provide current volume information of the therapeutic fluid in the drug reservoir without requiring direct contact of the therapeutic fluid with the pressure sensor.

20. A method of producing an implantable medical device comprising a volume measurement system, the method comprising:
providing an implantable medical device comprising a housing that defines a propellant chamber, and a drug reservoir positioned within the propellant chamber;
installing a volume measurement system in the implantable medical device, the volume measurement system comprising a temperature sensor configured to measure a temperature of a propellant gas within the propellant chamber and a pressure sensor configured to measure a pressure of the propellant gas within the propellant chamber;
charging the propellant chamber with a positive gauge pressure of the propellant gas; and
calibrating the volume measurement system so that the volume measurement system is configured to measure the pressure and the temperature of the propellant gas to provide current volume information of the therapeutic fluid in the drug reservoir;
wherein the volume measurement system is configured to measure the current volume of the therapeutic fluid based on the current volume of the propellant gas using the temperature and the pressure measured by the temperature sensor and the pressure sensor, wherein the current volume of the propellant gas is determined based on an ideal gas law;
wherein the volume measurement system is configured to measure the current volume of the therapeutic fluid based on Equation 4 below:

$$V_{Dr} = V_T - A\frac{T}{P} \quad \text{Equation 4}$$

wherein $V_{Dr}$ is the current volume of the therapeutic fluid having SI units of $m^3$, T is the temperature of propellant gas measured by the temperature sensor having SI units of K, P is the pressure of propellant gas measured by the pressure sensor having SI units of $J \cdot m^{-3}$, $V_T$ is a volume constant of the propellant chamber having SI units of $m^3$, and A is a gas constant of having SI units of $J \cdot K^{-1}$; and
wherein the volume measurement system is also configured to empirically determine at least A for calibrating the volume measurement system.

21. A method of determining a reservoir volume information of an implantable medical device, the method comprising:
providing an implantable medical device comprising a housing that defines a propellant chamber, and a drug reservoir positioned within the propellant chamber, a propellant gas within the propellant chamber, a volume measurement system comprising (i) a temperature sensor within the propellant chamber and not in direct contact with the therapeutic fluid and (ii) a pressure sensor, and processing circuitry connected to the volume measurement system;
measuring, using the processing circuitry, a current temperature of the propellant gas in the propellant chamber with the temperature sensor;

measuring, using the processing circuitry, a current pressure of the propellant gas in the propellant chamber with the pressure sensor; and determining, using the processing circuitry, current volume information of a therapeutic fluid in the drug reservoir based on the current temperature and the current pressure of the propellant gas in the propellant chamber.

22. The method of claim 21, wherein the pressure sensor is not in direct contact with the therapeutic fluid.

23. A method of determining a reservoir volume information of an implantable medical device, the method comprising:

providing an implantable medical device comprising a housing that defines a propellant chamber, and a drug reservoir positioned within the propellant chamber, a propellant gas within the propellant chamber, a volume measurement system comprising a temperature sensor and a pressure sensor, and processing circuitry connected to the volume measurement system;

measuring, using the processing circuitry, a current temperature of the propellant gas in the propellant chamber with the temperature sensor;

measuring, using the processing circuitry, a current pressure of the propellant gas in the propellant chamber with the pressure sensor; and determining, using the processing circuitry, current volume information of a therapeutic fluid in the drug reservoir based on the current temperature and the current pressure of the propellant gas in the propellant chamber;

wherein the volume measurement system is configured to measure a current volume of the therapeutic fluid based on Equation 4 below:

$$V_{Dr} = V_T - A\frac{T}{P} \qquad \text{Equation 4}$$

wherein $V_{Dr}$ is the current volume of the therapeutic fluid having SI units of $m^3$, T is the temperature of propellant gas measured by the temperature sensor having SI units of K, P is the pressure of propellant gas measured by the pressure sensor having SI units of $J \cdot m^{-3}$, $V_T$ is a volume constant of the propellant chamber having SI units of $m^3$, and A is a gas constant of having SI units of $J \cdot K^{-1}$.

* * * * *